United States Patent [19]

Adler

[11] Patent Number: 4,547,155
[45] Date of Patent: Oct. 15, 1985

[54] SHIELDED DENTAL CONTACT MARKER

[76] Inventor: Harold A. Adler, 1457 Eastwind Cir., Westlake Village, Calif. 91361

[21] Appl. No.: 590,198

[22] Filed: Mar. 15, 1984

[51] Int. Cl.$^4$ ................................................ A61C 9/00
[52] U.S. Cl. ...................................................... 433/70
[58] Field of Search ..................................... 433/70, 68

[56] References Cited

U.S. PATENT DOCUMENTS 2,633,637 4/1953 Lucia ...................................... 433/70
3,813,781 6/1974 Forgione ............................... 433/68

Primary Examiner—Robert Peshock

[57] ABSTRACT

Shielded dental contact marker has a thin, supple support layer which carries thereon a thin marker layer, such as carbon. A thin, hard protective shield layer of wax overlies the carbon layer. The shield layer is of such thickness and appropriate density as to compensate for periodontal ligament compression so that only forceful dental contact will penetrate the protective shield layer and only those points of forceful contact pressure between teeth are marked. The wax layer is sufficiently thin and hard that lateral shield layer flow does not smear or distort the mark on the dental surface.

8 Claims, 8 Drawing Figures

SHIELDED DENTAL CONTACT MARKER

BACKGROUND OF THE INVENTION

The field of this invention is that of dental devices, and in particular, to an improvement in the construction of a shielded dental contact marker that will mark exclusively surfaces that come into direct forceful contact, and leave unmarked areas of casual or close contact.

In order for teeth to function as an integral part of a masticatory apparatus, they must reduce food introduced into the mouth to small enough size to be mixed with saliva, comfortably swallowed, and efficiently acted on by digestive enzymes. The jaw muscles bring the movable lower jaw against the fixed upper jaw. The lower jaw, approximately L-shaped, has a ball and socket type of joint at the upper extremity of the "L", similar to the knee joint. The lower jaw describes a short arc in its movement about the fulcrum of this joint. The grinding surfaces of all teeth in each arch that work against teeth in the opposite arch must mesh together, or occlude. This brings together the maximum contacting surface of the teeth involved, and the posterior teeth are so shaped into peaks and valley, slopes and ridges, as to enhance the grinding and crushing action of these teeth on foods placed between them.

These raised areas on the teeth are subject to wear, from the abrasive action of some foods, acids, and from grinding against each other. The wear is irregular, and in response to this and other physiological activities, the teeth will frequently shift. These slight alterations in the surface anatomy of the teeth, and in their shifting, as well as irregularities in the growth formation, cause variations in the manner in which the teeth strike against each other and in the way they slide against each other. These variations of contact cause greater force to be exerted on some teeth and on different places on the peaks. Consequently, as the jaws bring these altered teeth into contact, the irregularities and changes of position cause individual teeth, or a few teeth, to come into premature contact, harder contact, interfere with sliding action, and prevent other teeth from coming into appropriate contact. Such interference to normal occlusion are generally called "prematurities," or "high spots."

Prematurities are areas of premature contact where a tooth or a few teeth make initial impact prior to the widely distributed contacts of normal occlusion, or where one or a few teeth bear the brunt of major pressures during tooth sliding movements.

Prematurities may also be man-made, and appear in all artificial teeth and fillings, whether they are "false teeth," silver or plastic fillings, gold inlays, procelain or gold crowns, or multiple crowns called "bridges." For whatever reasons they appear, prematurities are noxious to the healthful function of the teeth, jaws, muscles and joints. They must be reduced or removed by the dentist to bring about the normal relationship and funtion of the teeth and jaws. This is done by grinding, either on the natural teeth or artificial ones, whichever bear the offending places.

These prematurities and high spots are so small as to be unrecognizable by either patient or dentist. The dentist, therefore, must have some way to identify the offending surfaces, which are visually insignificantly tiny portions of the grinding surface of a tooth. The pain and discomfort they cause, however, are out of all proportion to their size. For the identification of the prematurities, or "high spots," the dentist uses articulating paper. The conventional form of articulating paper has a paper or polymer supporting layer upon which a marking layer of carbon or the like is attached. This is placed between the teeth, and the patient bites down against it and moves the teeth in biting and chewing motions. The material is trapped between the hard, raised tooth surfaces on opposite sides of it. As it is crushed between these raised surfaces, rubbed against, and struck, the pigment of the articulating material stains surfaces it contacts.

Unfortunately, the easily-transferred pigment also stains tooth surfaces that merely rub against it, as the carrier material may be suspended partly in a valley between two or more peaks, or cusps, or has been "dragged" over an upstanding peak, and not from actual firm contact between tooth surfaces. All marks that are not caused by the marking layer being forcibly crushed between opposing hard surfaces in forceful contact are called "false marks." Every articulating material in current and past use has the same major failing: all leave false marks, indistinguishable from true high spot marks. The dentist must grind them all in the attempt to remove the offending areas. Because of this, the process of removing prematurities is very wasteful of sound tooth structure, and also of both the dentists' and the patients' valuable time, not to mention the unnecessary discomfort caused to the patient by the unnecessary grinding of these "false marks."

SUMMARY OF THE INVENTION

In order to aid in the understanding of this invention, it can be stated in essentially summary form that it is directed to a shielded dental contact marker having a strong and supple support layer, a marker layer thereon, and a shield layer over the marker layer. The overall thickness is critically less than 0.006 inch with the protective wax shield layer critically less than 0.004 inch. The shield layer is sufficiently hard that it serves to prevent the marker layer from touching and staining those tooth surfaces that merely rub against the material, and it acts as a structural layer that compresses the periodontal membrane a few thousandths of an inch to hold the tooth solid so that penetration of the shield layer can occur to permit marking of the two surfaces.

It is, thus, an object and advantage of this invention to provide a shielded dental contact marker which has a shield layer upon a marker layer with the shield layer being sufficiently strong that the periodontal membrane is compressed to hold the tooth firmly in position while penetration of the hard wax shield layer can occur to permit marking of the tooth surface.

It is a further object and advantage of this invention to provide a shielded dental contact marker which has a total thickness of its support layer, marker layer and shield layer no more than 0.0006 inch and preferably in the range of 0.0015 to 0.0035 inch to provide consistent, accurate marking of the prematurities in the occlusion.

It is further object and advantage of this invention to provide a shielded dental contact marker which can be inexpensively produced, widely marketed, and have a long shelf life and which can be employed to more accurately mark the prematurities so that the dentist can provide better occlusion.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

DESCRIPTION OF THE PREFERRED EMBODIMENTS

The first preferred embodiment of the shielded dental contact marker of this invention is generally indicated at 10 in FIGS. 1, 2, 3, 4, 6 and 7. The shielded dental contact marker is made up of three layers of material. The support layer 12 is a film of material which is sufficiently strong as to not tear under normal usage, is sufficiently strong to handle, and is sufficiently pliable or supple so that the rigidity of the material does not change the manner in which marking is accomplished. Mylar is a presently preferred material, although there are a number of other tough, strong, flexible synthetic polymer composition material films. The thickness of the support layer 12 will be discussed below.

Marker layer 14 lies on support layer 12, over the entire area thereof. The marker layer 14 is made of any suitable material which stains by transfer. Carbon black in a suitable conventional carrier is the preferred material.

One of the critical aspects of the invention is the character of the shield layer 16. Shield layer 16 is a wax protective layer of proper hardness and proper thickness to permit marking of prematurities without marking of tooth surfaces which have not indented the shielded dental contact marker 10 with significant pressure. The shield layer 16 is a thin, hard wax layer which serves to prevent the marker layer from contacting the teeth from close, but casual or sliding contact. The preferred composition and range of materials in the marking layer are given in Table I.

TABLE I

|  | Weight Percentage | |
| --- | --- | --- |
|  | Preferred | Range |
| Paraffin wax | 50% | 50–60% |

TABLE I-continued

|  | Weight Percentage | |
| --- | --- | --- |
|  | Preferred | Range |
| Carnunba wax | 25 | 15–25 |
| Beeswax | 18 | 15–40 |
| Ceresin | 3 | 3–6 |
| Microcrystalline wax | 4 | 3–8 |

The thickness of both the marker layer and the shield layer are critical.

Figure 1:
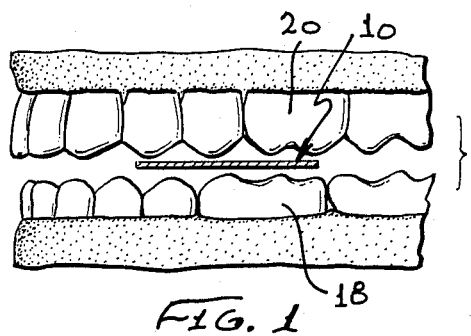
FIG. 1 shows the shielded dental contact marker of this invention positioned between teeth which are to be investigated for prematurities.
Figure 2:
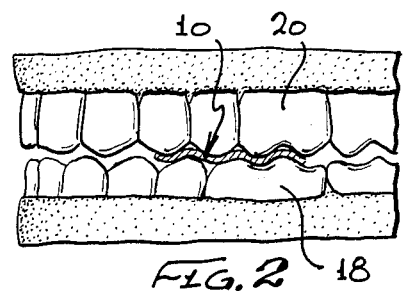
FIG. 2 shows the teeth closed upon the shielded dental contact marker of this invention to mark the prematurities on the teeth.
Figure 6:
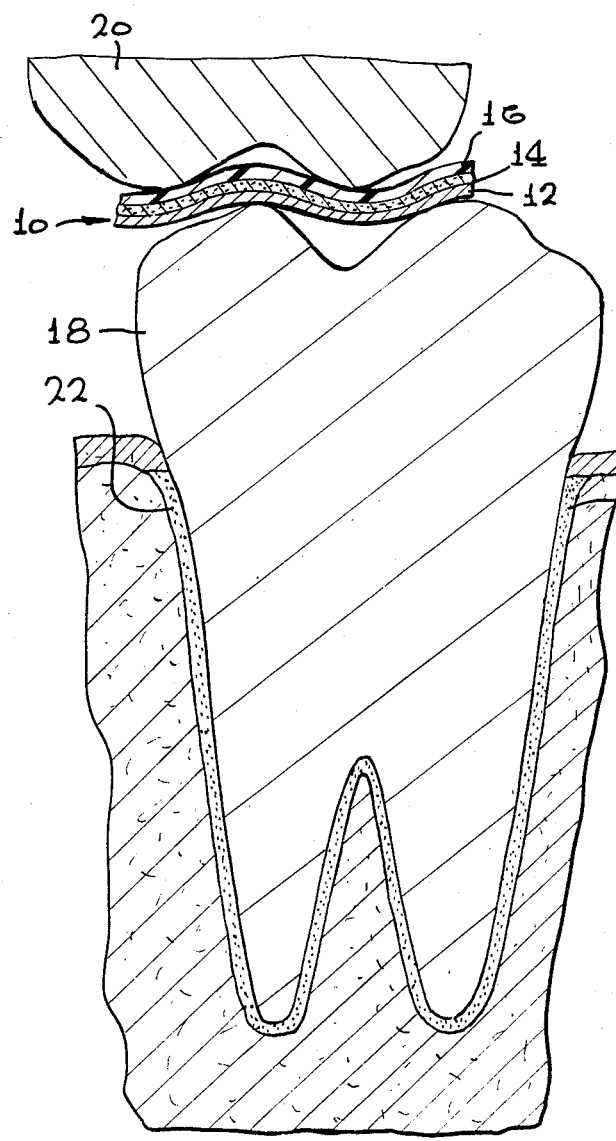
FIG. 6 is an enlarged front elevational view, with parts broken away, showing two teeth in first contact with the shielded dental contact marker of the embodiment shown in FIG. 4.
Figure 4:
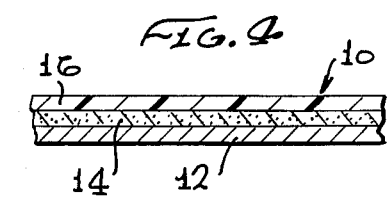
FIG. 4 is an enlarged cross section through the first preferred embodiment of the shielded dental contact marker of this invention, with parts broken away.

Human teeth are composed of the hard crown above the gum and the root surface below the gum, and held within the bone, which supports the crown portion. The root portion is separated from, but interconnected to, the bony material by the periodontal membrane, or periodontal ligament, as it is sometimes called. The periodontal membrane is mostly composed of fibers, which interconnect the root surface of the teeth with the bone that surrounds them. It is an elastic layer and acts to absorb the shock of hard tooth coming into forceful contact with other hard tooth surfaces, or solid foods caught between them. Without this "cushioning" effect of the periodontal membrane, the bone, as well as the crown and roots, would not survive the many-thousand-pound per square inch pressures of occlusion on each tooth. This structure is shown in FIG. 6 wherein tooth 18 of the lower jaw moves up toward occlusion with tooth 20 in the upper jaw. Periodontal membrane 22 surrounds and engages the roots of tooth 18 and attaches the tooth to the jawbone. The periodontal ligament itself is generally from 0.008 inch to 0.0016 inch. When compressed by about half of that dimension, much of the elasticity is removed so that the tooth is firmly seated when it moves into its socket about 0.004 to 0.008 inch, depending upon the individual tooth and the patient. When the shielded dental contact marker 10 of this invention is used, the hard protective shield layer forces the periodontal membranes of the opposing teeth to compress. Only after this elastic material is compressed is there sufficient resistance between the teeth for the prematurities to penetrate through the protective shield layer to contact the stain layer so that the stain can leave a contact mark on the tooth.

The overall thickness of the marker 10 is also critical. It has been found that when the total thickness exceeds 0.006 inch, the stain marks become more random as the thickness of the shield layer interferes with the occlusion of the teeth. With a total thickness between 0.004 and 0.006 inch, the material functions well and stains well, but somewhat less accurately than thinner material and interference of the thicker wax layer is felt between the teeth. The preferred range of total thickness is 0.0015 to 0.0035 inch. Materials in this range give consistent, accurate results. In this range, all of the variation is in the protective shield layer, with both the support layer and the marker layer of substantially 0.0005 inch thickness. It is thought that the minimum thickness at which the protective shield layer will give sufficient protection against inadvertent marking by the marker layer and provide sufficient resistance for periodontal membrane compression is about 0.0005 inch. These dimensions are given in the following Table II.

TABLE II

|  | Thickness (Inches) | | | |
| --- | --- | --- | --- | --- |
|  | Support | Marker | Shield | Total |
| Minimum | .00025 | .00025 | .0005 | .0010 |

TABLE II-continued

| | Thickness (Inches) | | | |
| --- | --- | --- | --- | --- |
| | Support | Marker | Shield | Total |
| Maximum | .001 | .001 | .004 | .006 |
| Preferred range | .0005 | .0005 | .0005–.0025 | .0015–.0035 |

Figure 7:
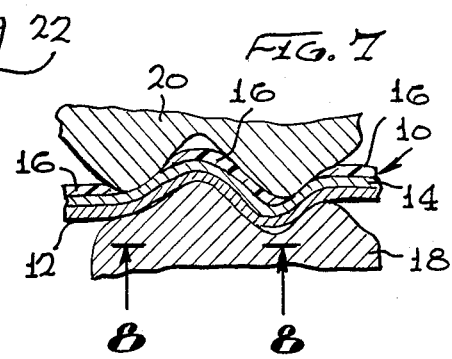
FIG. 7 is similar to FIG. 6, but showing the completion of marking of the teeth.
Figure 8:
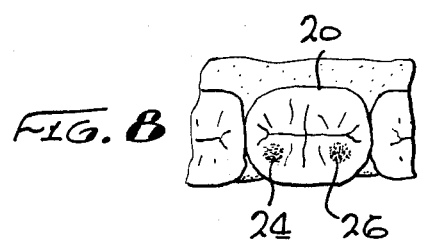
FIG. 8 is a plan view of reduced size showing a marked tooth, generally as seen along the line 8—8 of FIG. 7.
Figure 3:
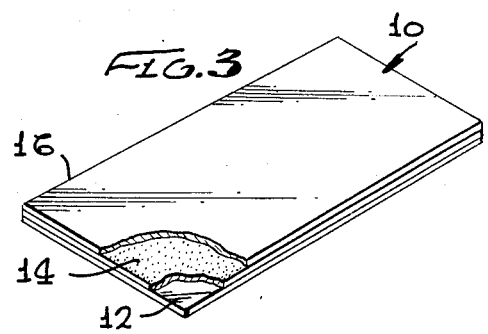
FIG. 3 is an isometric view of the shielded dental contact marker of this invention, with parts broken away and parts taken in section.

The shielded dental contact marker 10 is so thin and flexible that it does not inhibit the intermeshing of cusps and valleys of the teeth and the way the tooth surfaces move against each other. This is well illustrated in FIG. 2 where the teeth are shown as engaging on marker 10. The thin nature of the protective layer also has the advantage of providing little material that is thrust aside as the tooth penetrates to be marked. This prevents buildup of the non-penetrating areas. Such buildup of pressed-aside wax can interfere with proper occlusion. In addition, FIG. 7 shows the manner in which the protective shield layer 16 is penetrated by the prematurities on tooth 20 to cause areas 24 and 26 to be marked with material from the marker layer 14, see FIG. 8. The protective shield layer 16 provides better protection for the marker layer 14 than a thicker layer would. This result is because the protective shield layer 16 is so thin that it has sufficient flexibility that it flexes with the remainder of the marker 10. Additionally, because the protective shield layer 16 is sufficiently hard, lateral motion of the teeth over the surface (without significant pressure) permits the tooth to slide over the surface rather than cause a sliding and heap-up as would result if the protective layer were soft wax. In this way, a thin, semi-hard protective layer such as the wax layer described in Tables I and II gives complete protection to the marking layer from close, casual or sliding contact when the shielded dental contact marker is between opposing teeth.

In summary, the protective shield layer is structured to serve two critical and cooperative purposes. The protective shield layer 16 is non-sticky so that it slides across the two surfaces and is hard enough to maintain its layer when it merely rubs against two surfaces without significant pressure. However, the protective shield layer permits the penetration of the tooth surfaces when pressure is applied so that the two surfaces can reach the marker layer 14 to be appropriately marked. Thus, the protective shield layer is penetratable by the teeth when adequate pressure is applied. Such is the result when the total thickness is between the critical values of 0.001 and 0.006 inch, together with the appropriate hardness of the protective shield layer. The protective shield layer also acts as a structural member in compression during the beginning portion of dental contact. The protective layer is sufficiently hard or strong that the periodontal membrane is compressed a few thousandths of an inch before the tooth penetrates the protective shield layer so that the tooth is held solidly when the tooth penetration of the protective shield layer occurs to mark the tooth.

Figure 5:
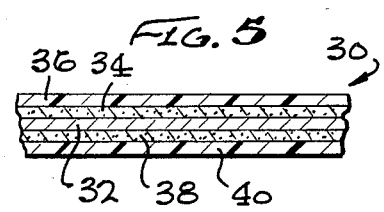
FIG. 5 is a section through a second preferred embodiment of the shielded dental contact marker of this invention, with parts broken away.

It is clear that the shielded dental contact marker 10 can mark the upper teeth when oriented as shown in FIGS. 3, 4, 6 and 7. It can be inverted to mark the lower teeth. In those cases where it may be desired to mark both the upper and lower occlusal surfaces at the same time, the shielded dental contact marker 30 illustrated in FIG. 5 can be employed. Marker 30 has a support layer 32, a marker layer 34, and a protective shield layer 36 which are the same as the layers 12, 14 and 16 illustrated in FIG. 4. In addition, marker layer 38 is attached to the underside of support layer 32 and protective shield layer 40 is attached thereto and positioned thereunder. The layers 38 and 40 are respectively identical to layers 14 and 16. When the marker 32 is placed between occlusal surfaces and the teeth are brought into contact therewith, sufficient pressure causes penetration of the tooth surfaces through both of the protective shield layers so that both the upper and lower occlusive surfaces are marked at the same time. The critical functions of protecting the marker layer and resisting penetration until the periodontal membrane is adequately compressed are both achieved with each of the protective shield layers in the same manner as the marker 10.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A penetration-resistant structurally-compressive shielded dental contact marker for marking
 a premature contact area between upper and lower teeth comprising:
 a very thin very flexible supporting layer;
 a very thin very flexible marking layer adhered to one side of said very thin very flexible supporting layer, said very thin very flexible marking layer to cause marking of a tooth only in that premature contact area which is in direct forceful contact with that tooth; and
 a very thin, very flexible, hard, low-flow under pressure protective layer of material permanently adhered to said very thin very flexible marking layer, said protective layer of material comprising a wax mixture composition including paraffin wax, carnauba wax, beeswax, ceresin and microcrystalline waxes in the ranges of: paraffin way—50 percent to 60 percent, carnauba wax 15 percent to 25 percent, beeswax—15 percent to 40 percent, ceresin—3 percent to 6 percent, and microcrystalline waxes—3 percent to 8 percent by weight; said very flexible penetration-resistant structurally-compressive layer having a required thickness of between 0.0005 and 0.004 inches and having the required physical characteristics of being hard non-sticky and very low flow under pressure so as to constitute a barrier sufficiently resistant during the beginning portion of forceful contact between approximating dental surfaces as to move with and give complete protection to said marking layer from close, casual or sliding contact with tooth surfaces and will prevent significant penetration by said approximating tooth surfaces until sufficient compressive force is applied in a direction normal to said supporting layer as will compress the periodontal membrane of the engaged teeth by about half thereby solidly seating the roots of said engaged teeth in their respective bony sockets, holding said teeth solidly upright, and only then permitting penetration through said specifically-structured pressure-selective shield material and solidly striking said very thin very flexible marking layer against said approximating tooth surface thereby marking it only at said specified-penetration areas, said very thin very flexible marking layer being otherwise continuously protected by said very thin very flexible pressure-selective protective shield layer against all other tooth contact.

2. The penetration-resistant, structurally-compressive very flexible shielded dental contact marker as defined in claim 1 wherein:

said structurally compression-selective very flexible protective shield layer comprises a hard wax mixture with a thickness between 0.0005 and 0.004 inches, and the total thickness of said shielded dental contact marker is between 0.001 and 0.006 inches.

3. The penetration-resistant, structurally-compressive very flexible shielded dental contact marker as defined in claim 1 wherein said composition of said structurally compression-selective very flexible protective layer essentially consists of the following:

paraffin wax—50 percent, carnauba wax—25 percent, beeswax—18 percent, ceresin—;b 3 percent, microcrystalline waxes—4 percent.

4. The penetration-resistant, structurally-compressive very flexible shielded dental contact marker as defined in claim 1 including:

a second very thin hard, very flexible structurally-compressive, non-interfering, selectively-protective layer of material adhered to said second very thin very flexible marking layer so that both upper and lower teeth are marked at said premature contact areas by said very thin very flexible marking layers, said second protective layer having a thickness between about 0.0005 and 0.004 inches.

5. A structurally-compressive, penetration-resistant shielded dental contact marker comprising:

a very thin very flexible support layer having a surface;

a very thin very flexible marker layer lying on said surface, said marker layer being suitable for marking dentition by contact therewith;

a very flexible structurally-compressive, penetration-resistant, non-interfering, selectively-protective shield layer lying on said marker layer, said protective layer of material comprising a wax mixture composition including paraffin wax, carnauba wax, beeswax, ceresin and microcrystalline waxes in the range of: paraffin wax—50 percent to 60 percent, carnauba wax 15 percent to 25 percent, beeswax—15 percent to 40 percent, ceresin—3 percent to 6 percent, and microcrystalline waxes—3 percent to 8 percent by weight; said protective shield layer being sufficiently hard so that casual contact of dentition therewith causes sliding of the protective marker layer over the dentition without significant distortion of said very flexible structurally compression-selective protective marker layer, said very flexible compression-selective, shielded non-interfering dental contact marker having a total thickness between 0.001 and 0.006 inch, said protective layer being cleanly penetrable by opposing tooth surfaces only when sufficient initial compressive force is applied in a direction normal to said supporting layer so as to compress the periodontal membrane of the engaged occlusal dentition by about half so that the surfaces of the occlusive dentition will penetrate said selectively-protective layer and become marked by said very thin marking layer only when the occlusive dentition is firmly seated in its periodontal membrane and bony sockets and the teeth are held solidly upright during the beginning portion of dental contact when said compressive force on said periodontal membrane has been exceeded and said specifically protective layer has been completely penetrated, said specifically protective layer to remain continuously with said very thin marking layer and will not readily flow under pressure, heap-up mold and adhere to the teeth so as to interfere with tooth contact and movement, said very-thin marking layer being continuously protected by said specifically-thin, very flexible, hard, low-flow, non-molding protective layer against penetration and markings other than permitted by the physical characteristics of said shield layer in other dental areas because of the specific barrier qualities of said selectively-protective shield layer against such false markings.

6. The very flexible structurally-compressive, non-interfering shielded dental contact marker of claim 5 wherein said compression-selective protective shield layer is between 0.0005 and 0.0040 inches thick.

7. The very flexible structurally-compressive, non-interfering shielded dental contact marker of claim 5 wherein said compression-selective protective shield layer is between 0.0015 and 0.0025 inches thick.

8. The very flexible structurally-compressive, non-interfering shielded dental contact marker of claim 5 wherein said compression-selective protective shield layer is sufficiently hard and of sufficient thickness so that the periodontal membrane of a particular tooth is sufficiently compressed during compression of the selectively-shielded dental contact marker between occlusal dentitions so that the particular teeth are firmly held upright as the dentition penetrates the pressure-selective protective shield layer with sufficient bite pressure to appropriately mark only the areas of premature tooth contact one those particular teeth.

* * * * *